(12) United States Patent
Kotaki et al.

(10) Patent No.: US 11,968,773 B2
(45) Date of Patent: Apr. 23, 2024

(54) CHARGED PARTICLE EMISSION CONTROL DEVICE, METHOD, AND PROGRAM

(71) Applicant: TOSHIBA ENERGY SYSTEMS & SOLUTIONS CORPORATION, Kawasaki (JP)

(72) Inventors: Kohei Kotaki, Inagi (JP); Munemichi Matsumoto, Fuchu (JP); Takuji Furukawa, Chiba (JP); Kota Mizushima, Chiba (JP)

(73) Assignee: TOSHIBA ENERGY SYSTEMS & SOLUTIONS CORPORATION, Kawasaki (JP)

( * ) Notice: Subject to any disclaimer, the term of this patent is extended or adjusted under 35 U.S.C. 154(b) by 227 days.

(21) Appl. No.: 17/646,822

(22) Filed: Jan. 3, 2022

(65) Prior Publication Data

US 2022/0132648 A1    Apr. 28, 2022

Related U.S. Application Data

(63) Continuation of application No. PCT/JP2020/025650, filed on Jun. 30, 2020.

(30) Foreign Application Priority Data

Jul. 4, 2019   (JP) ................. 2019-125124

(51) Int. Cl.
*A61N 5/10* (2006.01)
*H05H 13/04* (2006.01)

(52) U.S. Cl.
CPC ........... *H05H 13/04* (2013.01); *A61N 5/1048* (2013.01); *A61N 2005/1087* (2013.01)

(58) Field of Classification Search
CPC ........ H05H 5/1048; H05H 7/10; H05H 13/04; H05H 2277/11; A61N 5/10; A61N 5/1043;

(Continued)

(56) References Cited

U.S. PATENT DOCUMENTS 9,256,916 B2    2/2016  Omi
2006/0027766 A1*  2/2006  Matsuda ................. A61N 5/10
                                                  250/496.1

(Continued)

FOREIGN PATENT DOCUMENTS

EP    2 543 239 A1    1/2013
JP    2010-251106 A   11/2010

(Continued)

OTHER PUBLICATIONS

International Search Report dated Sep. 15, 2020 in PCT/JP2020/025650, filed on Jun. 30, 2020, 3 pages.

*Primary Examiner* — Tung X Le
(74) *Attorney, Agent, or Firm* — Oblon, McClelland, Maier & Neustadt, L.L.P.

(57) ABSTRACT

A charged particle emission control technique where slow extraction of a charged particle beam from a synchrotron can be stably performed even in a state where beam adjustment has not been performed or completed. A charged particle emission control device includes a first receiver configured to receive a first detection signal obtained by detecting a current value of charged particles orbiting in a synchrotron; an arithmetic processor configured to time-differentiate the first detection signal and output a beam-intensity equivalent-value; and an emission controller configured to output a control signal for emitting a charged particle beam from the synchrotron to a beam transport system in such a manner that the beam intensity-equivalent value matches a target value.

5 Claims, 5 Drawing Sheets

(58) Field of Classification Search
CPC .. A61N 5/1049; A61N 5/1067; A61N 5/1068; A61N 5/1077
See application file for complete search history.

(56) References Cited

U.S. PATENT DOCUMENTS

| | | | | |
|---|---|---|---|---|
| 2011/0266981 | A1* | 11/2011 | Umezawa | H05H 9/00 315/506 |
| 2012/0228493 | A1* | 9/2012 | Gottschalk | A61N 5/1075 250/306 |
| 2012/0274242 | A1* | 11/2012 | Haruna | H05H 7/02 315/504 |
| 2014/0330066 | A1* | 11/2014 | Fujii | A61N 5/1077 600/1 |
| 2015/0031931 | A1* | 1/2015 | Nishiuchi | A61B 6/4266 600/1 |
| 2017/0017232 | A1* | 1/2017 | Nishiuchi | G05B 19/0428 |
| 2018/0317311 | A1 | 11/2018 | Matsumoto et al. | |

FOREIGN PATENT DOCUMENTS

| | | |
|---|---|---|
| JP | 2012-234653 A | 11/2012 |
| JP | 2014-170714 A | 9/2014 |
| JP | 2017-112021 A | 6/2017 |
| JP | 2018-189465 A | 11/2018 |
| SG | 189670 A1 | 5/2013 |
| SI | 2 543 239 T1 | 11/2019 |
| TW | I507227 B | 11/2015 |
| WO | WO 2011/107120 A1 | 9/2011 |

* cited by examiner

CHARGED PARTICLE EMISSION CONTROL DEVICE, METHOD, AND PROGRAM

CROSS-REFERENCE TO RELATED APPLICATIONS

This application is a Continuation Application of No. PCT/JP2020/025650, filed on Jun. 30, 2020, and the PCT application is based upon and claims the benefit of priority from Japanese Patent Application No. 2019-125124, filed on Jul. 4, 2019, the entire contents of which are incorporated herein by reference.

TECHNICAL FIELD

Embodiments of the present invention relate to an emission control technique for charged particles orbiting a synchrotron.

BACKGROUND

In recent years, research has been carried out to apply a charged particle beam, which are brought into a high-energy state by supplying charged particles (ions) into an accelerator and accelerated them, to a wide range of fields such as engineering and medicine. Currently, a widely used accelerator system is roughly composed of an ion source, a linear accelerator (i.e., linac), and a circular accelerator (i.e., synchrotron), and stepwisely accelerates charged particles in this order. When the charged particles orbiting the synchrotron reach a predetermined energy, an emission control device is operated to extract the charged particle beam, traveling direction of which is changed from the orbit, to a beam transport system.

Specifications of emission control devices that extract a charged particle beam from a synchrotron are classified into fast extraction and slow extraction. The "fast extraction" is a method of extracting all the group (beam) of charged particles that orbit the synchrotron within the time required for one orbit.

The "Slow extraction" is a method of extracting a beam of charged particles little by little while causing the charged particles to orbit the synchrotron. Thus, as compared with the case of the "fast extraction", the charged particle beam to be obtained by the "slow extraction" can be gradually extracted over multiple orbits.

When the lesion is scanned and irradiated with the charged particle beam by using a particle beam therapy apparatus, it is necessary to extract the charged particle beam from the synchrotron such that the fluctuation of the beam intensity is small. In order to monitor that a charged particle beam of stable intensity is supplied to the beam transport system, a beam intensity monitor is provided in at least one of the irradiation port of the treatment room and the beam transport system, and the beam intensity of the charged particles is detected. This detected value is fed back to the emission control device, and the beam intensity of the charged particles to be extracted from the synchrotron is appropriately controlled such that this detected value becomes a preset value.

PRIOR ART DOCUMENT

Patent Document

[Patent Document 1] JP 2017-112021 A

SUMMARY

Problems to be Solved by Invention

When the accelerator system and the particle beam therapy apparatus are installed on site or their system maintenance is performed, adjustment work of various devices is performed. This adjustment work may be performed while the charged particle beam is being slowly extracted from the synchrotron. However, until the adjustment of the beam transport system is completed, the charged particle beam does not reach monitor, which is provided in the beam transport system or the irradiation port of the treatment room, in some cases. In such a case, in the above-described known technique, the feedback control does not function, and thus, the slow extraction of the charged particle beam from the synchrotron cannot be stably performed.

One of the adjustment contents of the beam transport system is a beam adjustment work of adjusting the current value of the electromagnet such that the charged particle beam passes through the center in the duct and the beam size becomes the target value. Hence, if the slow extraction of the charged particle beam, beam intensity of which is controlled to be constant, cannot be stably performed, there is a problem that the adjustment work becomes extremely difficult and the adjustment time becomes long.

In view of the above-described circumstances, an object of embodiments of the present invention is to provide a charged particle emission control technique by which slow extraction of a charged particle beam from a synchrotron can be stably performed even in a state where beam adjustment has not been performed or completed.

DETAILED DESCRIPTION

First Embodiment

Figure 1:
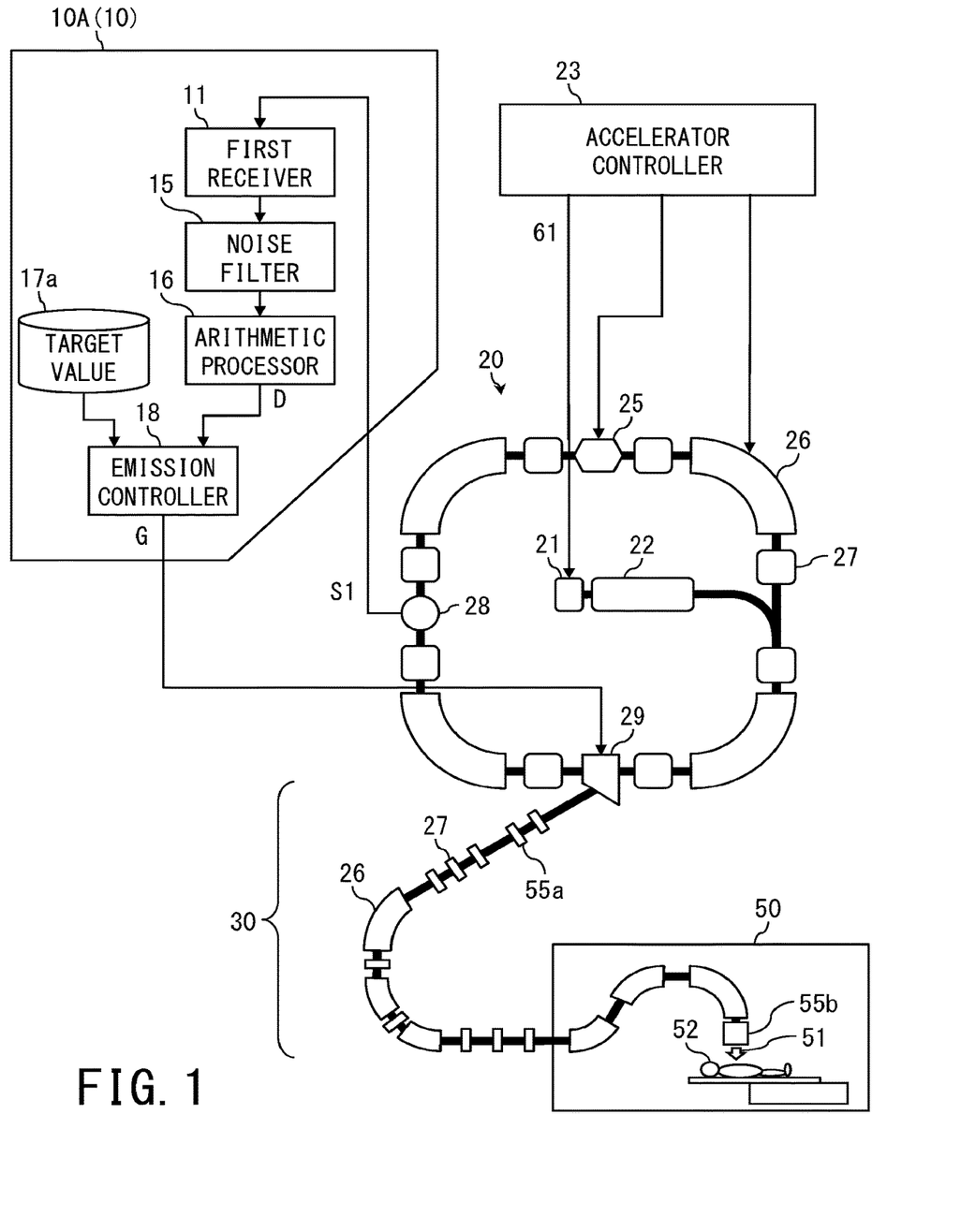
FIG. 1 is a block diagram of a charged particle emission control device according to the first embodiment of the present invention.

Hereinafter, embodiments of the present invention will be described by referring to the accompanying drawings. FIG. 1 is a block diagram of a charged particle emission control device 10A (hereinafter, simply referred to as "emission control device 10A") according to the first embodiment of the present invention. The emission control device 10A (10) includes: a first receiver 11 configured to receive a first detection signal S1 that is a detected current value of the charged particles orbiting in a synchrotron 20; an arithmetic processor 16 that performs calculation including at least time differentiation on the first detection signal S1 and outputs a beam-intensity equivalent-value D; and an emission controller 18 configured to output a control signal G for emitting a charged particle beam 51 from the synchrotron to a beam transport system 30 in such a manner that the beam-intensity equivalent-value D matches a target value 17a.

The emission control device 10A (10) further includes a noise filter 15 that is connected to the input stage of the time differentiation on the first detection signal S1 in the arithmetic processor 16 and removes the noise component contained in the first detection signal S1. An amplifier (not shown) configured to amplify the first detection signal S1, which is an analog signal, is also provided at the input stage of the noise filter 15. Although the amplified first detection signal S1 is then processed by the noise filter 15 and the arithmetic processor 16 as an analog signal in some cases, the amplified first detection signal S1 is processed by the noise filter 15 and the arithmetic processor 16 after being converted into a digital signal in some cases.

Since the noise component is removed from the first detection signal S1 in this manner, the accuracy of the differential processing in the arithmetic processor 16 is enhanced, and thus, consistency between beam intensity of the charged particle beam 51 and the beam-intensity equivalent-value D is improved as described below. The arithmetic processor 16 may set the time differential value of the first detection signal S1 to the beam-intensity equivalent-value D. Additionally, the value obtained by multiplying the time differential value of the first detection signal S1 by a conversion coefficient may be used as the beam-intensity equivalent-value D.

The accelerator system is composed of an ion source 21, a linac 22, and the synchrotron 20, and in this order, the charged particles are stepwise accelerated. When the charged particles orbiting the synchrotron 20 reach a predetermined energy, an emission device 29 is operated while this predetermined energy is being maintained, and the charged particle beam 51, traveling direction of which is changed from the orbit, is extracted to the beam transport system 30. In this description, energy means energy per nucleon.

Although aspects of the ion source 21 include a high-frequency (including microwave) irradiation type such as an ECR (Electron Cyclotron Resonance) ion source and a PIG (Penning Ionization Gauge) ion source in addition to a laser irradiation type ion source, the ion source 21 is not limited to them.

The linac 22 arranges a plurality of accelerating electric fields with opposite electric field components next to each other into a straight line, repeatedly inverts the electric field direction at a high frequency, and always accelerates the charged particles passing through the accelerating electric field in only one direction. The linac 22 accelerates the ions having been made incident from the ion source 21 to a predetermined energy and then emits the ions to the synchrotron 20.

The synchrotron 20 includes: a high-frequency acceleration cavity 25 configured to accelerate the charged particles having been made incident from the linac 22 by high-frequency power; a plurality of bending electromagnets 26 configured to generate magnetic fields that give centripetal force to the orbiting charged particles 26; a plurality of quadrupole electromagnets 27 configured to generate a magnetic field that diverges and converges the orbiting charged particles and holds them in the orbit; a current detector 28 configured to detect the current value of the beam of orbiting charged particles 28; and the emission device 29 configured to emit a beam of charged particles orbiting the synchrotron 20 to the beam transport system 30 little by little.

The synchrotron 20 configured as described above can accelerate the beam of the charged particles having been made incident from the linac 22 at low energy to the upper limit energy, which is 70% to 80% of the speed of light, while causing the beam to keep orbiting. The synchrotron 20 can hold the energy of the beam of orbiting charged particles at any energy lower than this upper limit energy. The accelerator controller 23 controls the ion source 21, the linac 22 and the synchrotron 20 in conjunction with each other such that the beam of the charged particles described above is accelerated correctly.

The beam transport system 30 is also provided with: the quadrupole electromagnets 27 for keeping the charged particles traveling straight in the orbit; and the bending electromagnets 26 for applying centripetal force to the charged particles to bend the orbit. An irradiation device 50 configured to irradiating a patient's tumor with the charged particle beam 51 as treatment is connected to the output stage of this beam transport system 30. The irradiation device 50 is only one aspect, and the facility to be connected to the output stage of the beam transport system 30 is not particularly limited.

The specification of the emission device 29 adopted in the embodiment is the "slow extraction" in which a group (beam) of charged particles orbiting the synchrotron 20 is gradually extracted. The emission device 29 excites the emission electrode (not shown) on the basis of the control signal G inputted from the emission control device 10 so as to extract the beam transitioned to an unstable region from the synchrotron 20 to the beam transport system 30.

The beam transport system 30 is provided with a beam intensity monitor 55a and the irradiation device 50 is provided with a beam intensity monitor 55b so that the beam intensity of the charged particle beam 51 can be monitored.

FIG. 2A to FIG. 2E are timing charts illustrating emission control of charged particles according to the embodiment. At the timing shown in FIG. 2A, the command signal 61 is transmitted from the accelerator controller 23 (FIG. 1) to the ion source 21. Thereby, the charged particles are outputted from the ion source 21, accelerated by the linac 22, and then a beam of the charged particles is supplied to the synchrotron 20.

Figure 2A:
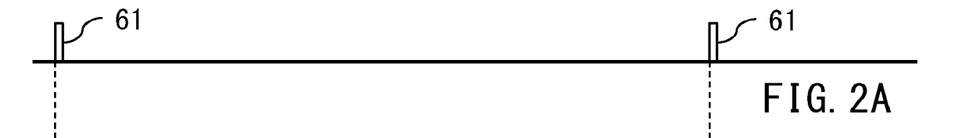
FIG. 2A to FIG. 2E are timing charts illustrating emission control of charged particles according to the embodiment.
Figure 2B:
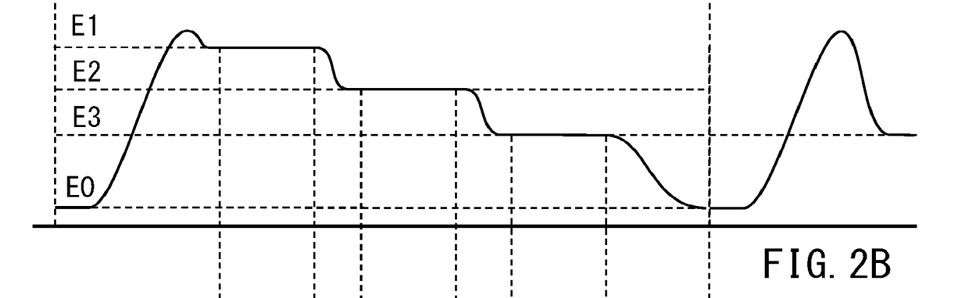

FIG. 2B shows the profile of the exciting current to be applied to the bending electromagnets 26 from the accelerator controller 23 (FIG. 1). Since the exciting current of the bending electromagnets 26 is a value to be uniquely determined depending on the energy of the orbiting charged particles, FIG. 2B may be considered to show the energy profile of the charged particles orbiting the synchrotron 20.

Before the command signal 61 is transmitted, the synchrotron 20 is set to the initial state that is appropriate for orbiting the charged particles having an incident energy $E_0$ immediately after being supplied from the linac 22. After the beam of the charged particle is made incident, the synchrotron 20 changes the setting state into the direction of increasing the energy of the charged particles, and holds the setting state when the energy becomes stable at the predetermined energy $E_1$.

Figure 2C:
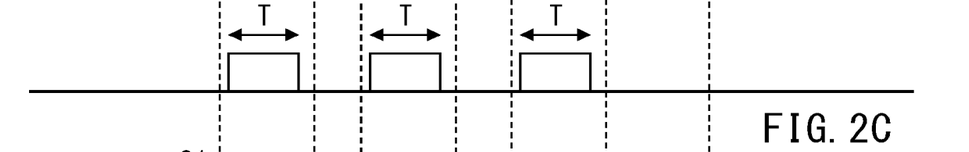

FIG. 2C shows the period T of the control signal G to be transmitted from the emission control device 10 (FIG. 1) to the emission device 29 under the state where the setting state of the synchrotron 20 is held at the energy $E_1$ (or $E_2$, $E_3$). In this manner, in the period T during which the control signal G is transmitted to the emission device 29, the beam of the charged particles orbiting the synchrotron 20 is gradually extracted to the beam transport system 30.

Figure 2D:
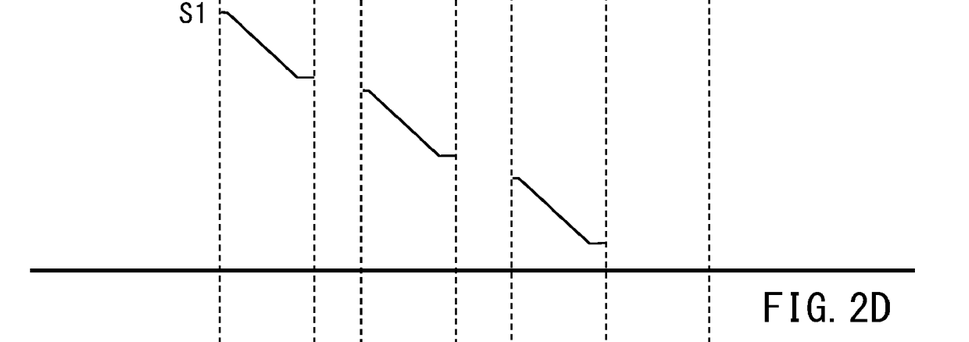
Figure 2E:
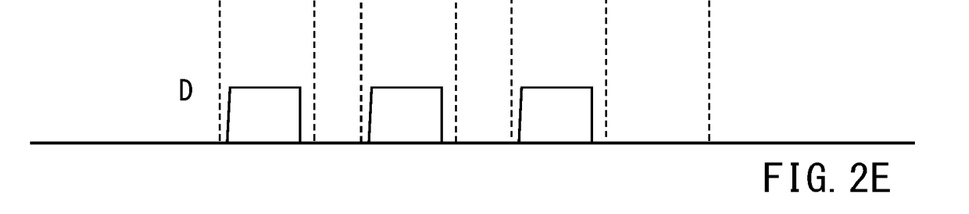

FIG. 2D shows the profile of the first detection signal S1 that is a current value of the beam of the charged particles orbiting the synchrotron 20 and is detected by the current detector 28 (FIG. 1). FIG. 2E shows the profile of the beam-intensity equivalent-value D obtained by time-differentiating the first detection signal S1 in the arithmetic processor 16 (FIG. 1).

If the beam is adjusted properly and there is no loss, the number of the charged particles passing through the beam transport system 30 matches the decrease in the number of the charged particles orbiting the synchrotron 20. Thus, the beam-intensity equivalent-value D corresponds to the beam intensity of the charged particle beam 51 extracted to the beam transport system 30.

Hence, when control is performed such that the beam-intensity equivalent-value D of the first detection signal S1 is fed back from the synchrotron 20 so as to match the target value 17a (FIG. 1), the control signal G, which is for the charged particle beam 51 and stabilizes the beam intensity, can be generated in the emission controller 18. In this manner, the beam of charged particles can be gradually extracted from the synchrotron 20 to the beam transport system 30. In addition, the energy setting state of the synchrotron 20 can be stepwise changed like $E_1$, $E_2$, and $E_3$.

With the elapse of time T during which the control signal G is transmitted to the emission device 29, the beam of the charged particles orbiting the synchrotron 20 diminishes or disappears. Thus, the setting state of the synchrotron 20 is returned (decelerated) from the energy $E_1$, $E_2$, $E_3$ to the state of the incident energy $E_0$ (i.e., state of the initial setting), the command signal 61 is transmitted to the ion source 21 again, and a new beam of the charged particles is supplied to the synchrotron 20. Note that the reduced beam of the preceding charged particles goes out of the orbit and disappears completely in this deceleration process.

The setting state of the synchrotron 20 can be held at any level below the upper energy limit. Thus, the beam of the newly supplied charged particles can be stably held in the states of different energies $E_1$, $E_2$, $E_3$. In this manner, the system repeats a series of processes of: supplying a beam of the charged particles to the synchrotron 20; accelerating it; emitting the charged particle beam 51 to the beam transport system 30; decelerating the beam of the charged particles; and supplying the beam of the charged particles to the synchrotron 20 again.

Second Embodiment

Figure 3:
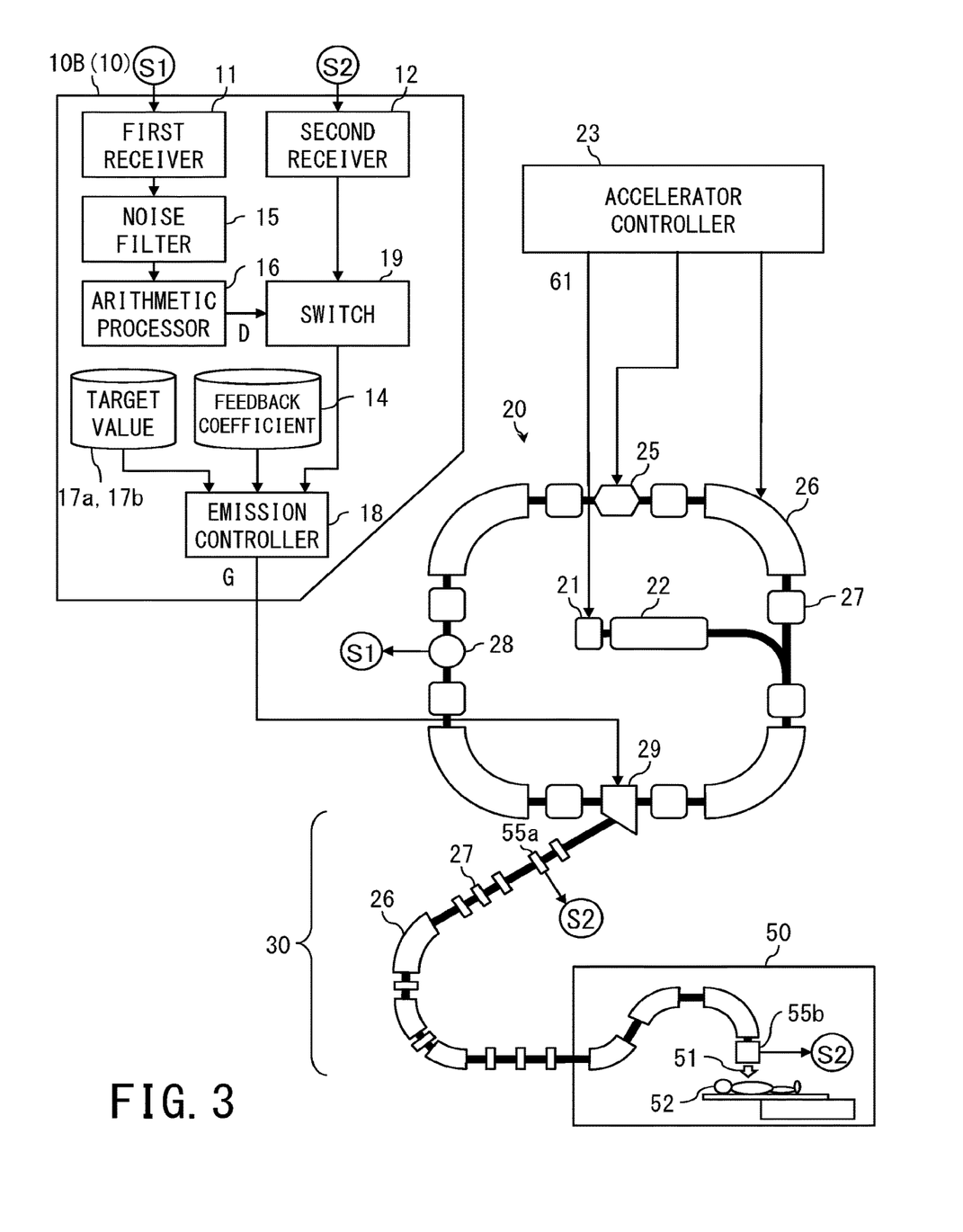
FIG. 3 is a block diagram of a charged particle emission control device according to the second embodiment.

FIG. 3 is a block diagram of a charged particle emission control device 10B (hereinafter, simply referred to as "emission control device 10B") according to the second embodiment. In FIG. 3, components having the same configuration or function as those in FIG. 1 are denoted by the same reference signs, and duplicate description is omitted.

In addition to the configuration of the emission control device 10A, the emission control device 10B (10) of the second embodiment further includes: a second receiver 12 configured to receive a second detection signal S2 that is obtained by detecting the intensity of the charged particle beam 51 having been emitted to the beam transport system 30; and a switch 19 that switches between the inputted beam-intensity equivalent-value D and the second detection signal S2 so as to output one of both. The emission controller 18 outputs the control signal G for emitting the charged particles from the synchrotron 20 to the beam transport system 30 such that the second detection signal S2 matches the target value 17b. The switch 19 may also be able to switch between receiving the output of the beam intensity monitor 55a and receiving the output of the beam intensity monitor 55b, for the second detection signal S2.

At this time, in the emission control device 10B, the feedback coefficient 14 required for the output of the control signal G is also switched in conjunction with the switching between the beam-intensity equivalent-value D and the second detection signal S2. The intensity of the charged particle beam 51 emitted to the beam transport system 30 can be detected by using the beam intensity monitors 55a and 55b.

In the first embodiment, the control signal G to be transmitted to the emission device 29 is generated on the basis of the beam-intensity equivalent-value D of the first detection signal S1 of the current value of the beam of the charged particles orbiting the synchrotron 20. The emission control of the charged particle beam 51 according to the first embodiment is considered to be sufficient for the adjustment work of various devices constituting the beam transport system 30 but remains uncertain in terms of accuracy as the charged particle beam 51 to be radiated onto the patient 52.

Thus, during treatment of the patient 52, the feedback target is changed by the switch 19 from the beam-intensity equivalent-value D of the first detection signal S1 of the beam current value to the second detection signal S2 of the intensity of the charged particle beam 51. As a result, the charged particle beam 51 to be actually radiated onto the patient 52 can be further stably controlled.

Figure 4:
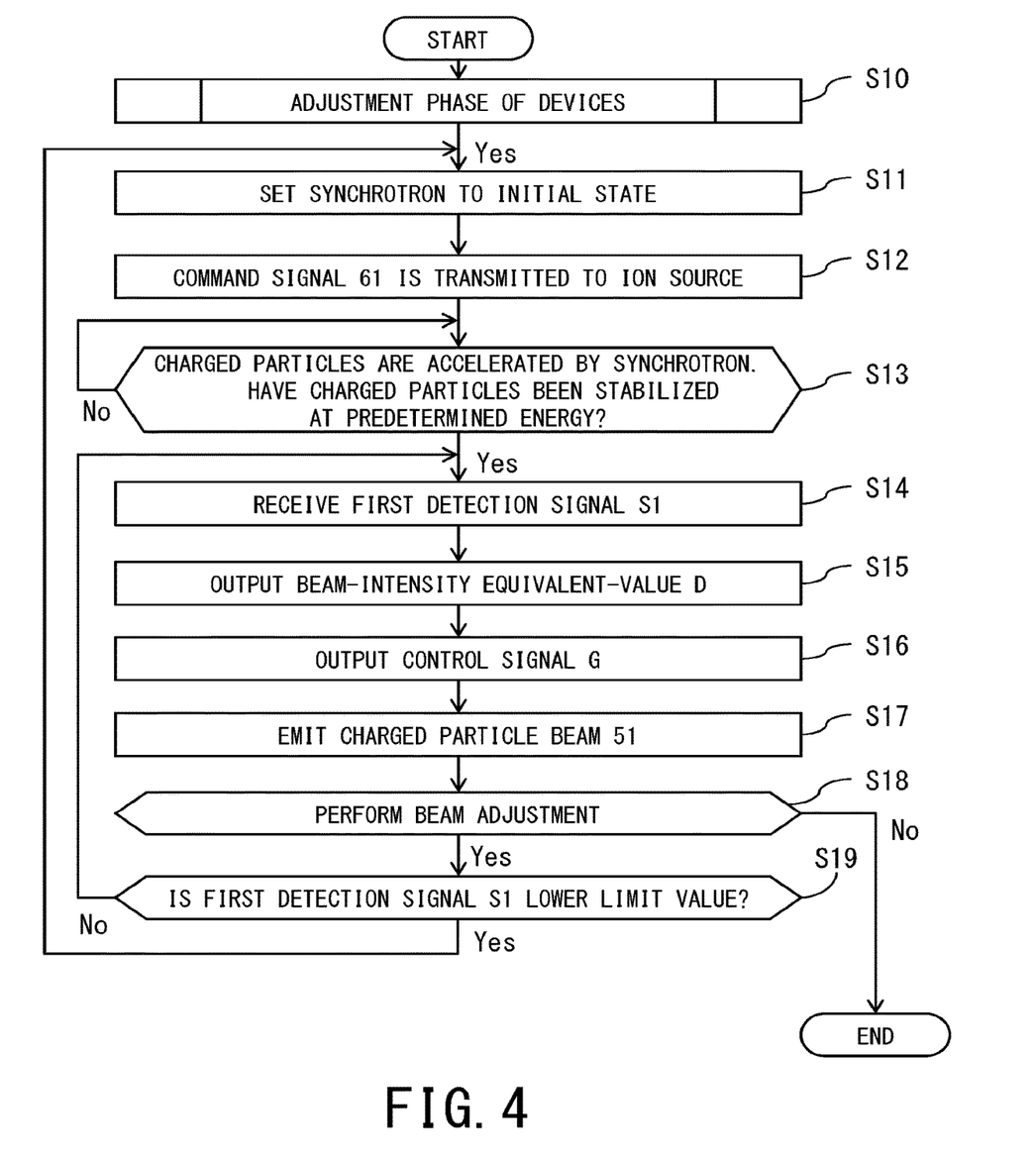
FIG. 4 is a flowchart illustrating a charged particle emission control method and a charged particle emission control program according to the first embodiment.

FIG. 4 is a flowchart illustrating a charged particle emission control method and a charged particle emission control program according to the first embodiment (refer to FIG. 1 and FIG. 2 as required).

First, as the adjustment phase (step S10) of the devices constituting the beam transport system 30, the synchrotron 20 is set to the initial state in the step S11. In the step S12, the command signal 61 for outputting the charged particles is transmitted to the ion source 21.

Consequently, the beam of the charged particles is accelerated by the linac 22 and supplied to the synchrotron 20. Further, the beam of the charged particles is accelerated by the synchrotron 20 and stabilized at a predetermined energy in the step S13.

In the next step S14, the first detection signal S1, which is obtained by causing the current detector 28 to detect the current value of the beam of the charged particles orbiting the synchrotron 20, is received.

In the step S15, the beam-intensity equivalent-value D obtained by time-differentiating this first detection signal S1 is outputted.

In the next step S16, the control signal G, which is generated by feeding back the beam-intensity equivalent-value D to match the target value 17a, is outputted to the emission device 29.

In the step S17, the charged particle beam 51 is emitted from the synchrotron 20 to the beam transport system 30.

In the step S18, beam adjustment is performed while the charged particle beam 51 is being emitted to the beam transport system 30 in this manner. In some cases, the beam adjustment is performed by gradually changing the energy setting state of the synchrotron 20 such as $E_1$, $E_2$, and $E_3$.

If the beam of the charged particles orbiting the synchrotron 20 decreases and the first detection signal S1 outputted by the current detector 28 reaches the lower limit value in the step S19, the synchrotron 20 is returned to the initial state and the flow from the steps S11 to S19 is repeated.

If the beam adjustment is completed (No in the step S18), the flow is completed (END).

Figure 5:
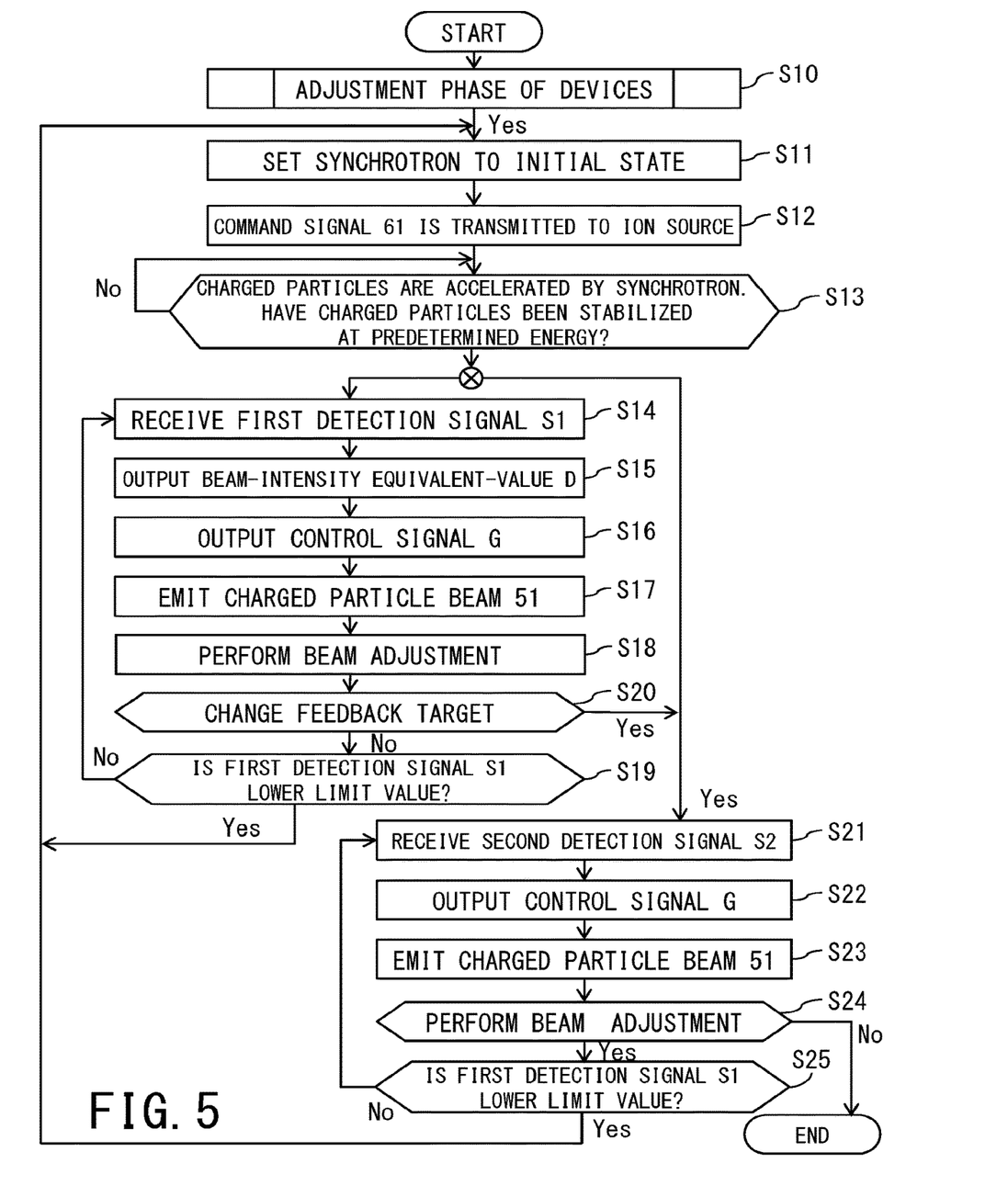
FIG. 5 is a flowchart illustrating a charged particle emission control method and a charged particle emission control program according to the second embodiment.

FIG. 5 is a flowchart illustrating a charged particle emission control method and a charged particle emission control program according to the second embodiment (refer to FIG. 1 and FIG. 2 as required).

In addition to the flow from the steps S11 to S19 of the first embodiment, the flow of the second embodiment further includes: the step S20 in which the feedback target is changed from the first detection signal S1 to the second detection signal S2 by operating the switch 19 (FIG. 3); and the steps S21 to S25.

After the feedback target is changed to the second detection signal S2 (Yes in the step S20), while the charged particle beam 51 is being emitted to the beam transport system 30, the intensity of the charged particle beam 51 detected by the beam intensity monitor 55a or 55b is received as the second detection signal S2 in the step S21.

In the next step S22, the control signal G, which is generated by feeding back the second detection signal S2 to match the target value 17b, is outputted to the emission device 29.

In the step S23, the charged particle beam 51 is emitted from the synchrotron 20 to the beam transport system 30.

In the step S24, beam adjustment is performed while the charged particle beam 51 is being emitted to the beam transport system 30 in this manner.

If the beam of the charged particles orbiting the synchrotron 20 decreases and the first detection signal S1 outputted by the current detector 28 reaches the lower limit value in the step S25, the synchrotron 20 is returned to the initial state (steps S11 to S13), and then the flow from the steps S21 to S25 is repeated.

If the beam adjustment is completed (No in the step S24), the flow is completed (END).

The charged particle emission control device of at least one embodiment described above can stably perform slow extraction of a charged particle beam from a synchrotron by feeding back a differential value of a current value of charged particles orbiting the synchrotron even in the state where beam adjustment has not been performed or completed.

While certain embodiments have been described, these embodiments have been presented by way of example only, and are not intended to limit the scope of the inventions. These embodiments may be embodied in a variety of other forms, and various omissions, substitutions, and changes may be made without departing from the spirit of the inventions. These embodiments and their modifications are included in the accompanying claims and their equivalents as well as included in the scope and gist of the inventions.

Further, the components of the charged particle emission control device can be realized by a computer processor and can be operated by a charged particle emission control program.

The above-described charged particle emission control device includes: a controller with highly integrated processors such as a dedicated chip, an FPGA (Field Programmable Gate Array), a GPU (Graphics Processing Unit), and a CPU (Central Processing Unit); a memory such as a ROM (Read Only Memory) and a RAM (Random Access Memory); an external storage device such as a HDD (Hard Disk Drive) and a SSD (Solid State Drive); a display; an input device such as a mouse and a keyboard; and a communication I/F, and can be realized by a hardware configuration using a normal computer.

In addition, the program to be executed by the charged particle emission control device is provided by incorporating the program into a ROM or the like in advance. Additionally or alternatively, this program may be provided as a file in an installable or executable format stored in a computer-readable storage medium such as a CD-ROM, a CD-R, a memory card, a DVD, and a flexible disk (FD).

Further, the program to be executed by the charged particle emission control device according to the present embodiment may be provided by being stored on a computer connected to a network such as the Internet and then being downloaded via the network. Moreover, the device can also be configured by interconnecting separate modules, which independently perform the respective functions of the components, via a network or a dedicated line and using them in combination.

The invention claimed is:

1. A charged particle emission control device comprising:
   a first receiver configured to receive a first detection signal obtained by detecting a current value of charged particles orbiting in a synchrotron;
   an arithmetic processor configured to perform calculation including at least time differentiation on the first detection signal and output a beam-intensity equivalent-value;
   an emission controller configured to output a control signal for emitting a charged particle beam from the synchrotron to a beam transport system in such a manner that the beam-intensity equivalent-value matches a target value;
   a second receiver configured to receive a second detection signal obtained by detecting intensity of the charged particle beam emitted to the beam transport system; and
   a switch configured to switch whether the beam-intensity equivalent-value or the second detection signal is inputted to the emission controller,
   wherein, when the second detection signal is inputted, the emission controller outputs the control signal for emitting the charged particle beam from the synchrotron to the beam transport system in such a manner that the second detection signal matches the target value.

2. The charged particle emission control device according to claim 1, further comprising a noise filter configured to remove a noise component included in the first detection signal before performing the time differentiation.

3. The charged particle emission control device according to claim 1, wherein a feedback coefficient required for output of the control signal is switched in conjunction with switching between the beam-intensity equivalent-value and the second detection signal.

4. A charged particle emission control method comprising steps of:
   receiving a first detection signal obtained by detecting a current value of charged particles orbiting in a synchrotron;
   performing calculation including at least time differentiation on the first detection signal to output a beam-intensity equivalent-value;
   outputting a control signal for emitting a charged particle beam from the synchrotron to a beam transport system in such a manner that the beam-intensity equivalent-value matches a target value;
   receiving a second detection signal obtained by detecting an intensity of the charged particle beam emitted to the beam transport system; and switching whether the beam-intensity equivalent-value or the second detection signal is inputted to the emission controller, wherein, when the second detection signal is received, outputting the control signal for emitting the charged particle beam from the synchrotron to the beam transport system in such a manner that the second detection signal matches the target value.

5. A charged particle emission control program that allows a computer to perform:

a reception process of receiving a first detection signal obtained by detecting a current value of charged particles orbiting in a synchrotron;

a calculation process of performing calculation including at least time differentiation on the first detection signal to output a beam-intensity equivalent-value;

an output process of outputting a control signal for emitting a charged particle beam from the synchrotron to a beam transport system in such a manner that the beam-intensity equivalent-value matches a target value;

a reception process of receiving a second detection signal obtained by detecting intensity of the charged particle beam emitted to the beam transport system; and a switch process of switching whether the beam-intensity equivalent-value or the second detection signal is inputted to the emission controller, wherein, when the second detection signal is received, the output process outputs the control signal for emitting the charged particle beam from the synchrotron to the beam transport system in such a manner that the second detection signal matches the target value.

* * * * *